United States Patent
Hart et al.

(10) Patent No.: US 6,231,572 B1
(45) Date of Patent: May 15, 2001

(54) ELECTROSURGICAL CATHETER APPARATUS AND METHOD

(75) Inventors: Charles C. Hart, Huntington Beach; Nabil Hilal, Mission Viejo; Richard C. Ewers, Huntington Beach; Bounsavanh Pravongviengkham, Corona, all of CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 09/087,361

(22) Filed: May 29, 1998

(51) Int. Cl.[7] .................................................. A61B 18/14
(52) U.S. Cl. .............................. 606/45; 606/41; 606/48; 606/159; 606/194; 607/99
(58) Field of Search .................................. 606/41, 45, 46, 606/47, 48, 113, 159, 194; 607/99, 113, 116

(56) References Cited

U.S. PATENT DOCUMENTS

| | | | |
|---|---|---|---|
| 5,024,617 | * | 6/1991 | Karpiel .................................. 606/47 |
| 5,196,024 | * | 3/1993 | Barath .................................. 606/159 |
| 5,891,136 | * | 4/1999 | McGee et al. ........................ 606/41 |
| 5,904,679 | * | 5/1999 | Clayman ............................... 606/39 |

FOREIGN PATENT DOCUMENTS

| | | | | |
|---|---|---|---|---|
| 2209676 | * | 5/1989 | (GB) | ................................... 607/116 |
| 91/17717 | * | 1/1991 | (WO) | ................................... 606/45 |

* cited by examiner

Primary Examiner—Lee Cohen
(74) Attorney, Agent, or Firm—Richard L. Myers, Esq.

(57) ABSTRACT

A catheter adapted to increase the patency of a body conduit includes an elongate tube having an axis extending between a proximal end and a distal end, and a balloon disposed at the distal end of the tube and having properties for being expanded to a high-profile state and for being contracted to a low-profile state. A sleeve disposed over the balloon has a pair of ends disposed on opposing sides of a central section, the ends having a floating relationship relative to the tube with the central section disposed circumferentially of the balloon. An electrode disposed outwardly of the sleeve has properties for being electrosurgically energized to incise materials defining the body conduit when the balloon is in the high-profile state. The electrode can be formed of a plurality of elements stranded to increase the surface area of the electrode. The catheter can be inserted relative to a guide member having a conductor which carries the electrosurgical energy from the proximal end of the tube to the electrode at the distal end of the tube. An associated method includes the step of introducing electrosurgical energy into the conductor of the guide member to energize the electrode of the catheter.

20 Claims, 12 Drawing Sheets

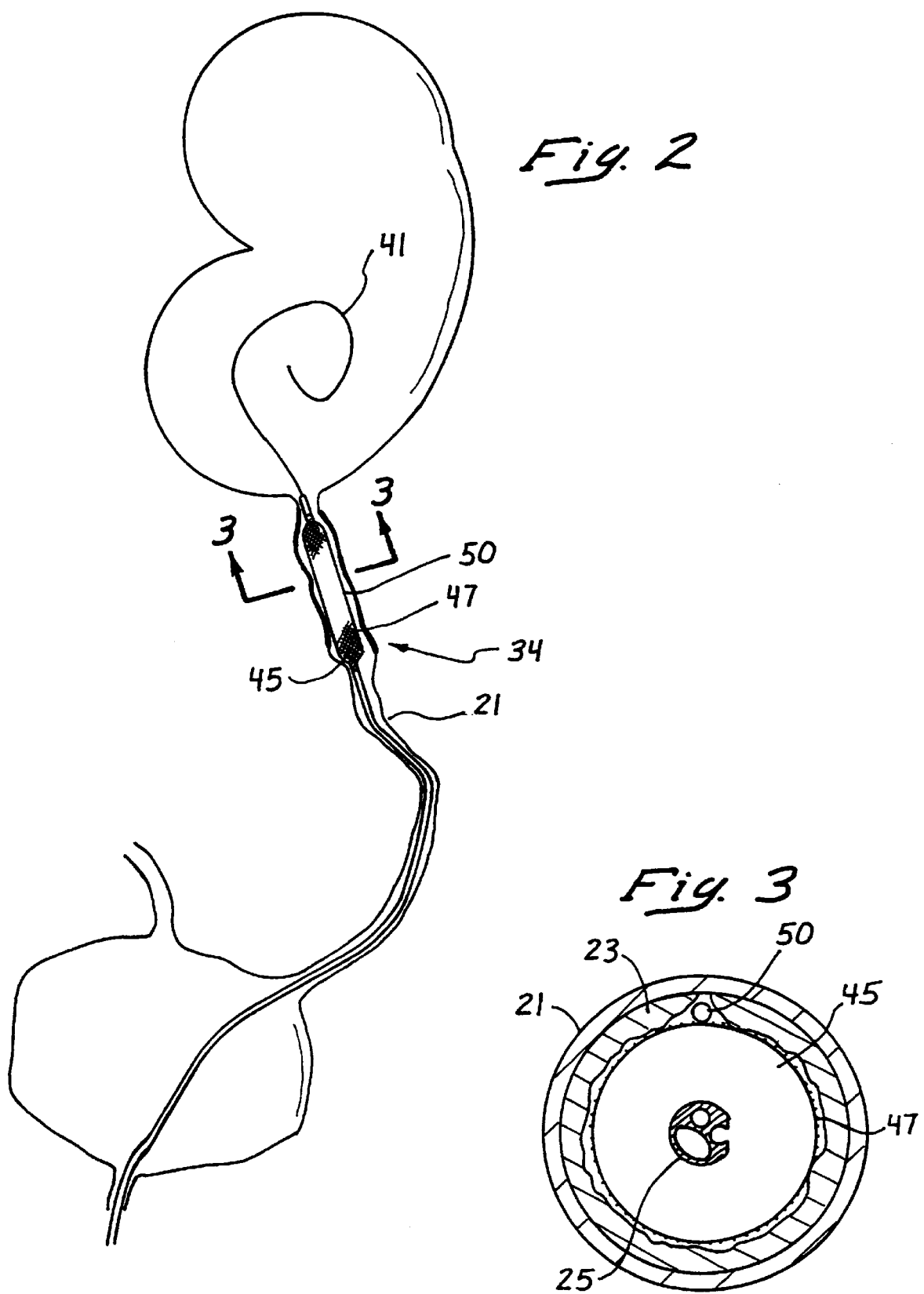

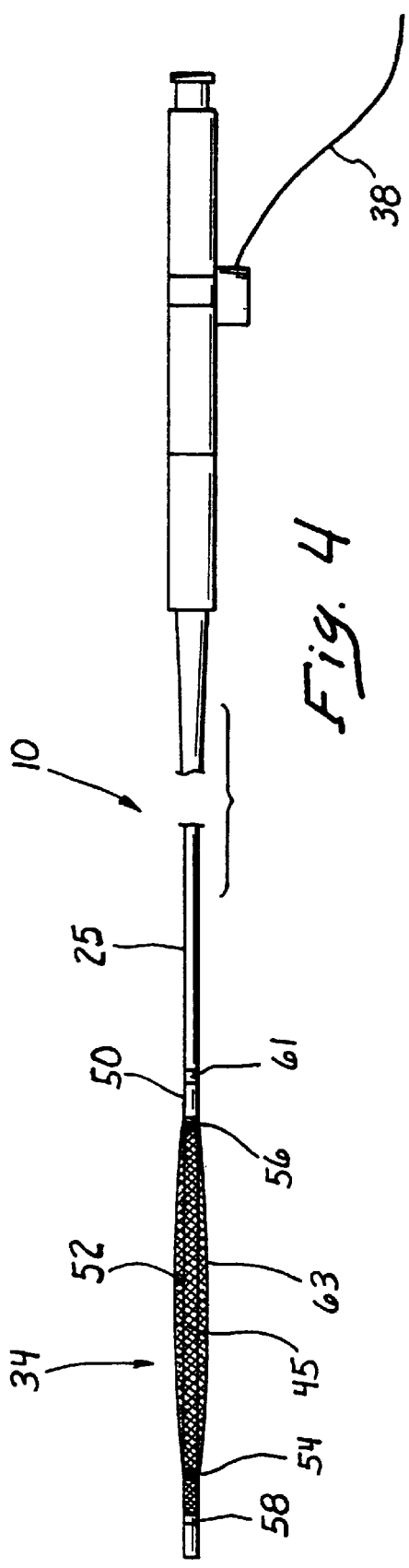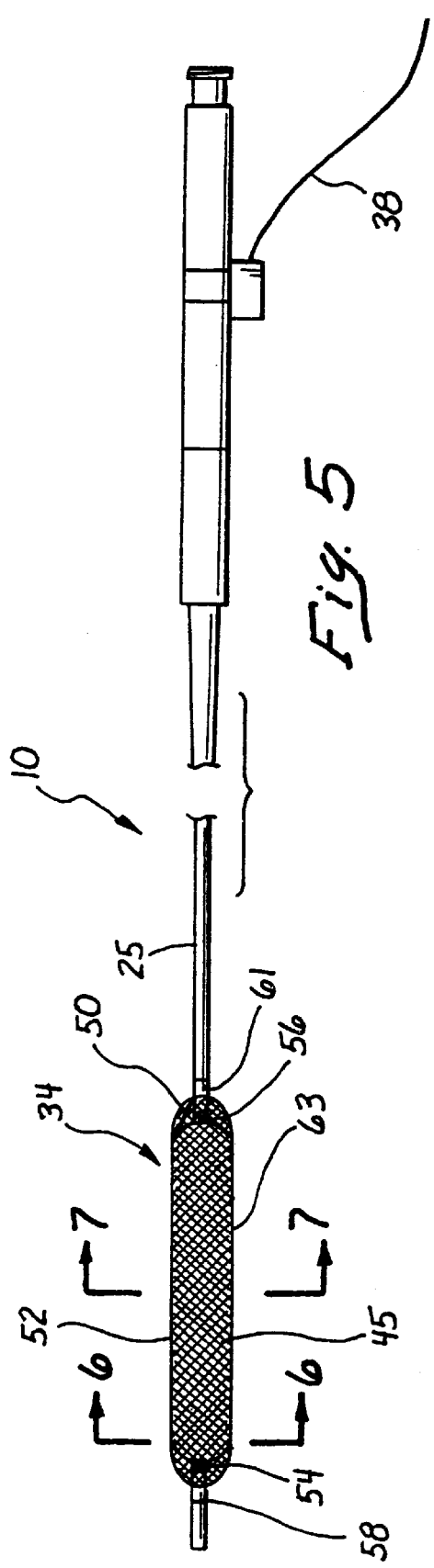

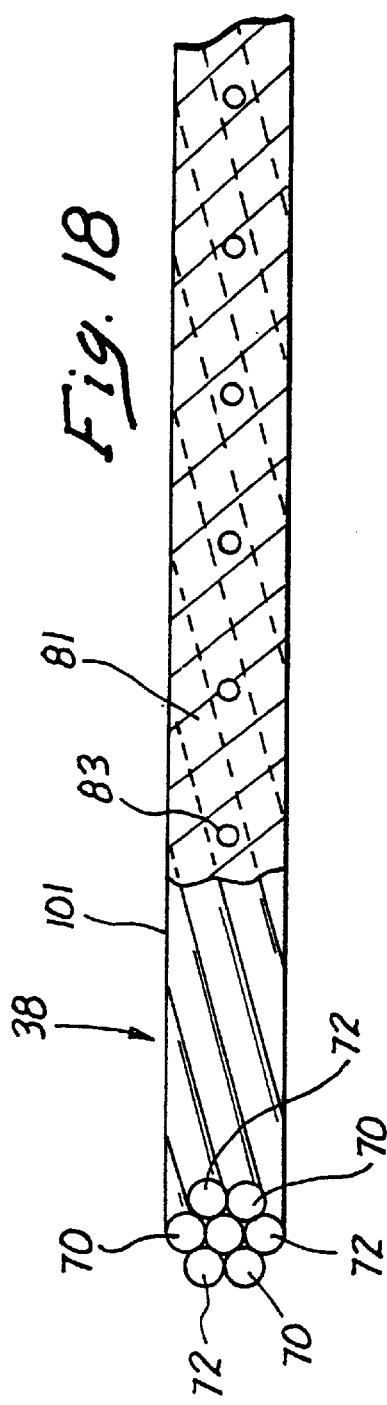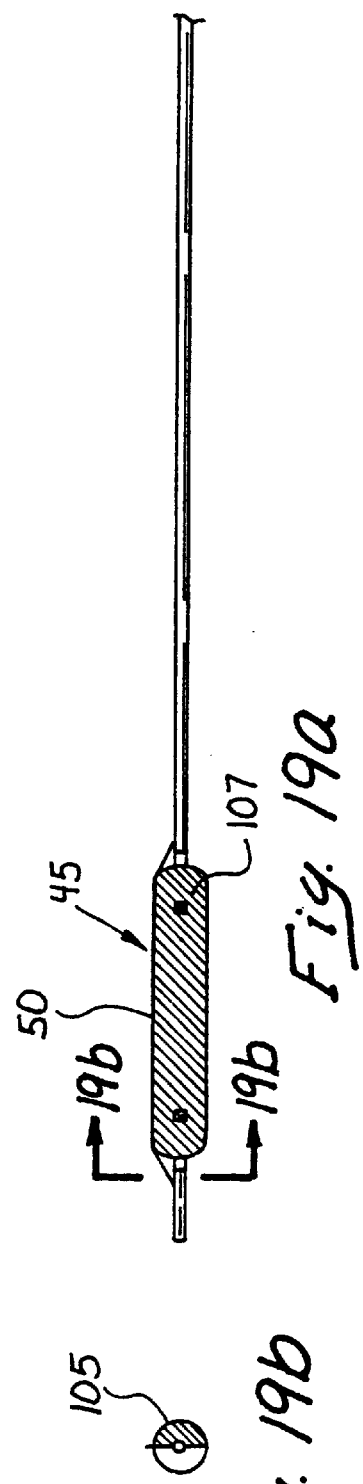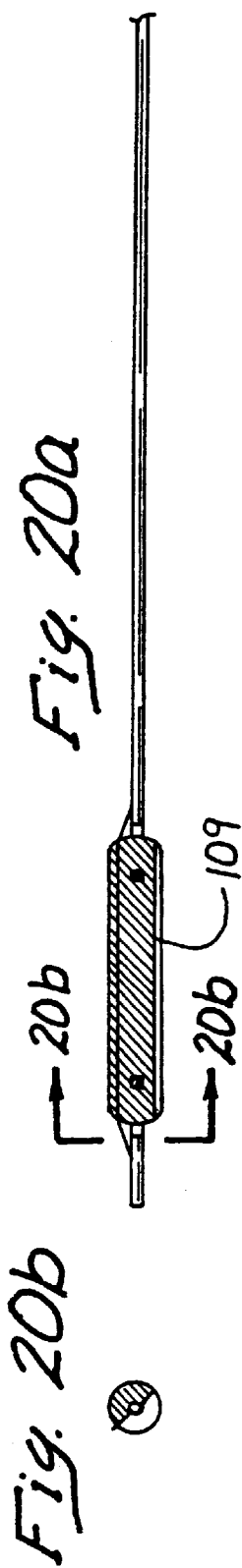

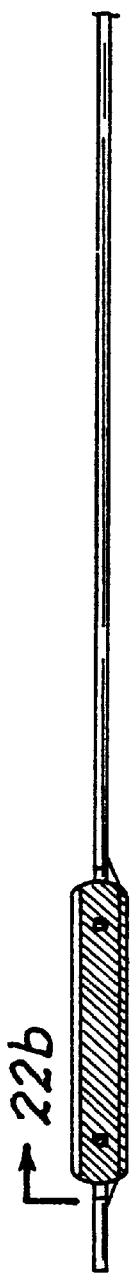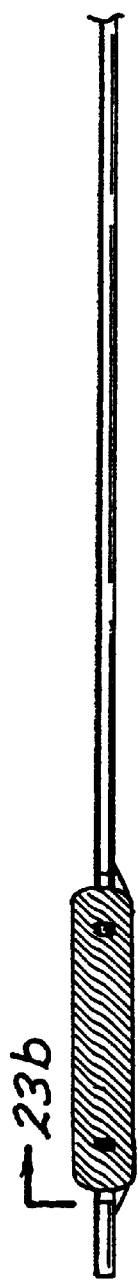

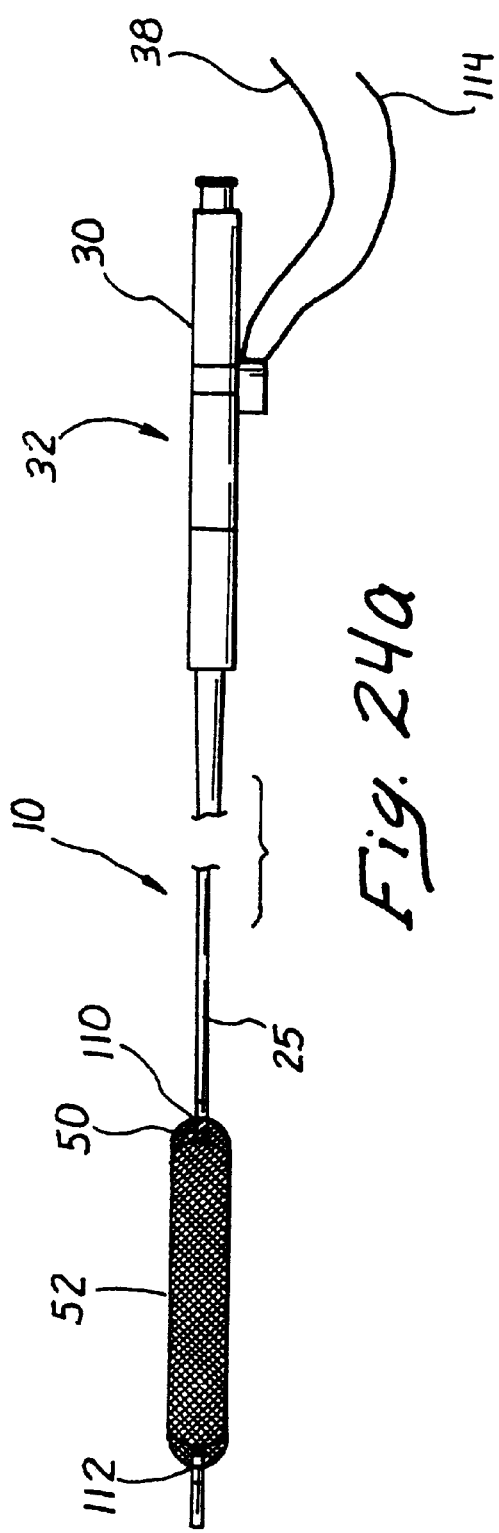
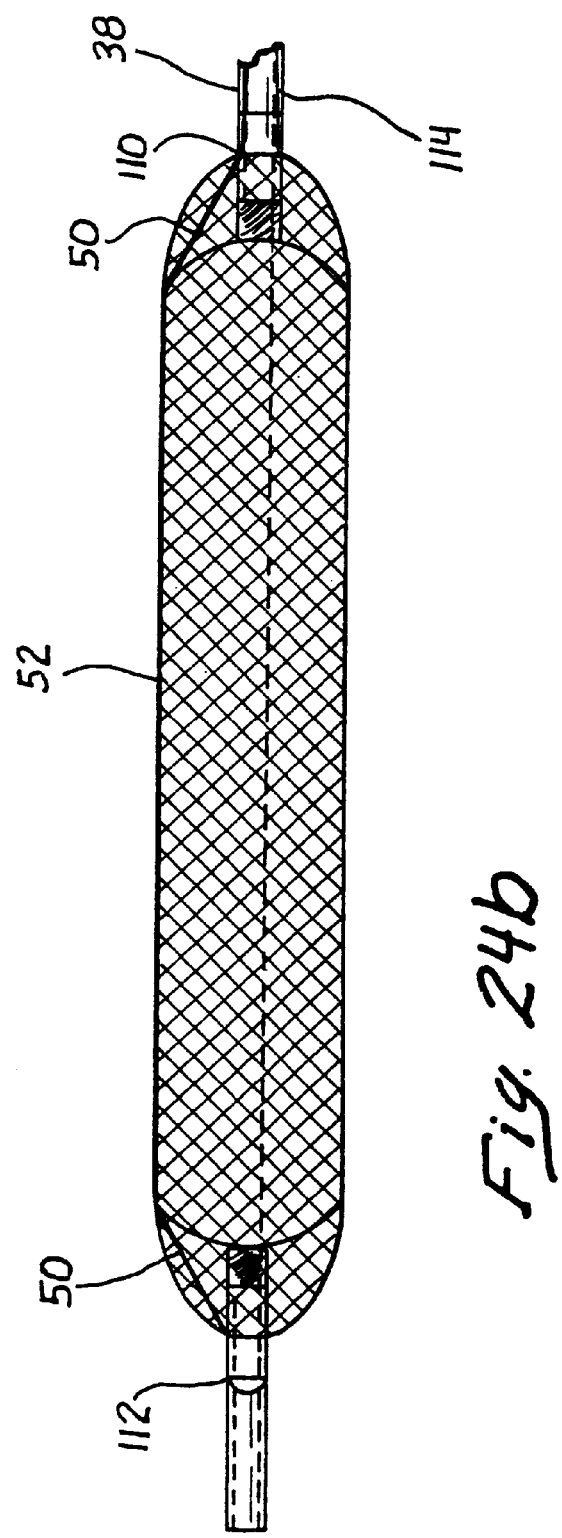
Fig. 24a
Fig. 24b

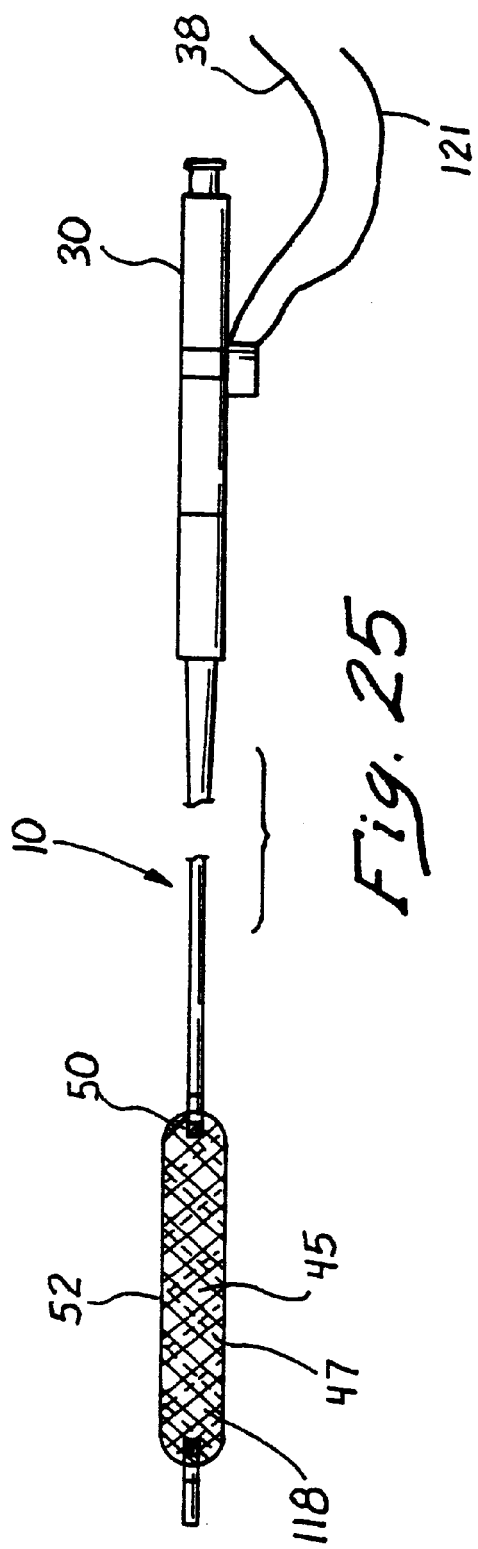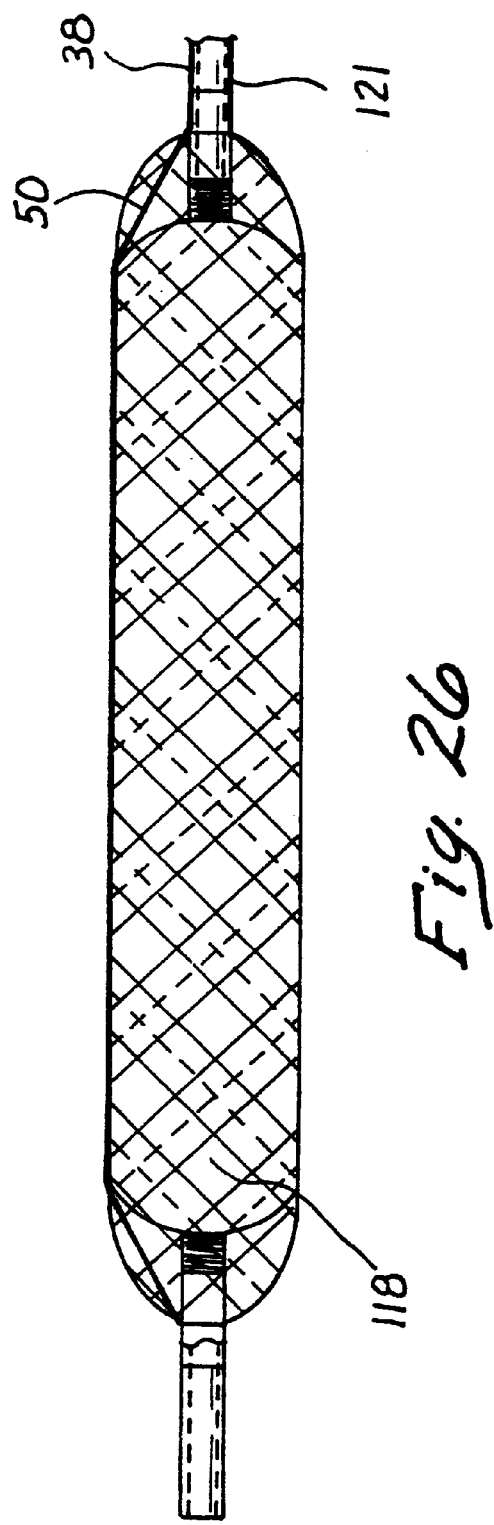

ELECTROSURGICAL CATHETER APPARATUS AND METHOD

BACKGROUND OF THE INVENTION

1. Field of the Invention

This invention relates generally to surgical devices and more specifically to electrosurgical catheters adapted to incise body material defining a body conduit.

2. Discussion of the Prior Art

Various surgical devices have been used to electrosurgically ablate or otherwise cut body materials. In this type of surgery, electrosurgical energy is passed between two electrodes creating a high current density which ablates the body materials. In a typical monopolar system, the patient is coupled to a large grounding pad which forms one of the electrodes. The electrosurgical device forms the other electrode. In this system, the electrosurgical device provides a very low surface area and consequently a very high current density for ablation or cutting in proximity to the device. In a bipolar system, the two electrodes are included in the device and high current density is achieved in the small area between the electrodes.

These electrosurgical devices include a catheter having a balloon and an electrode extending over the surface of the balloon as disclosed in applicant's co-pending applications, Ser. No. 08/241,007, filed on May 11, 1994, and entitled "Angioplasty Catheter and Method for Making Same", and Ser. No. 08/216,512, filed on Mar. 22, 1994, and entitled "Improved Catheter with Electrosurgical Cutter". The entirety of this disclosure is incorporated herein by reference. This catheter is used in a monopolar system where an electrode, in the form of a wire, is disposed over a radially expandable balloon of the catheter. As the balloon is inflated, the electrode is carried radially outwardly into proximity with the body material to be ablated or cut. Although it has always been of interest to increase the current density associated with the wire electrode, this has been difficult to achieve as smaller wire sizes necessarily result in reduced electrode strength and integrity. The balloon material has also been restricted to insure against over-expansion and electrode proximity. Materials forming non-distensible balloons have been preferred, but have made it difficult to achieve a low-profile state for insertion.

SUMMARY OF THE INVENTION

In accordance with the present invention, an electrosurgical catheter is provided with a balloon and an electrode extending axially along the outer surface of the balloon. A sleeve is disposed over the balloon and provided with ends which float along the catheter body between a low-profile state and a high-profile state for the sleeve. In the high-profile state, the sleeve has a predetermined maximum diameter which limits the radial dimension of the balloon. Portions of the electrode extend through the sleeve to facilitate the electrosurgical function. The sleeve can also be provided with characteristics whereby the sleeve is biased to its low-profile state further facilitating a minimal profile for the catheter. The sleeve will typically be manufactured of a thermoplastic or thermoset material.

The sleeve can be formed from a plurality of elements which are woven, braided, or otherwise stranded to form an expandable structure. The electrode may form one of these elements in the sleeve. The electrode may also be formed from elements which are stranded to increase the surface area of the electrode without increasing its diameter. The electrode, the balloon, or the sleeve can be coated with an insulation to control the electrical relationships between these elements.

For example, the electrode can be formed of stranded elements which provide the electrode with an outer surface having peaks and valleys. Portions of this insulation can be removed to expose the elements in a straight or curved pattern. The electrode can be connected at each of its ends through conductors to the proximal end of the catheter thereby facilitating increased current flow to the electrode.

In another embodiment, the guidewire can be provided with an electrically conductive core which is exposed through insulation to energize the electrode at the distal end of the catheter. Using the guidewire as a conductor eliminates the need for an additional conductor in the catheter to energize the electrode. The conductive guidewire also facilitates operative disposition of the catheter at the surgical site.

In a semi-bipolar system, either the balloon or the sleeve can be used as a second electrode replacing the grounding pad in a typical monopolar system. With the wire forming one of the electrodes, the metalized balloon or sleeve forms the other electrode in a semi-bipolar system. This system provides the advantage of current density at the wire, but does not require electrical current to be conducted throughout the body of the patient. The electrosurgical current need only flow from the active electrode with a minimal surface area to the balloon or sleeve which provide a high-surface area.

In one aspect of the invention, a catheter is adapted to increase the patency of a body conduit and comprises an elongate tube having an axis extending between a proximal end and a distal end. A balloon is disposed at the distal end of the tube and provided with properties for being expanded to a high-profile state and for being contracted to a low-profile state. A sleeve is disposed over the balloon and provided with a pair of ends which define a central section of the sleeve. The ends of the sleeve are disposed to floatingly engage the tube with the central section disposed circumferentially of the balloon. An electrode includes portions disposed outwardly of the sleeve and having properties for being electrosurgically energized to incise the body materials and increase the patency of the body conduit.

In another aspect of the invention, the electrode is formed of a plurality of elements stranded between a proximal end and a distal end to provide the electrode with an elongate configuration.

In a further aspect of the invention, the electrode has a radial cross-section which is non-circular in configuration.

In a further aspect of the invention, a guide member is adapted to facilitate insertion of a catheter into a body conduit. The guide member includes a core extending along an axis between a proximal end and a distal end, the core having properties for conducting energy. Insulation is disposed over the core with a portion of the insulation defining an exposed portion of the core at the proximal end of the guidewire and at the distal end of the guidewire.

In a further aspect of the invention, a combination includes the guide member and a catheter with an elongate shaft adapted to be moved along the guide member. An electrode disposed along the catheter is coupled to an exposed conductive core of the guide member to permit passage of energy from the proximal end of the guidewire along the core to the electrode at the distal end of the catheter.

These and other features and advantages of the invention will be more apparent with a description of preferred embodiments and reference to the associated drawings.

DESCRIPTION OF THE DRAWINGS

FIG. 2 is an enlarged plan view with the distal end of the catheter disposed in the upper pelvic junction of the ureter;

FIG. 3 is a radial cross-section view taken along lines 3—3 of FIG. 2;

FIG. 4 is a side elevation view of the catheter with its distal end in a low-profile state;

FIG. 5 is a side elevation view similar to FIG. 4 with the distal end of the catheter illustrated in a high-profile state;

FIG. 18 is a perspective view of a further embodiment of the electrode similar to FIG. 10 wherein multiple elements are stranded and individually energizable to control conductivity through associated windows in the insulation;

FIG. 19a is a side-elevation view illustrating the balloon partially metalized to facilitate a semi-bipolar operation and visual radial orientation of the electrode;

FIG. 19b is a cross-section view taken along lines 19b—19b of FIG. 19a;

FIG. 20a is a side-elevation view similar to FIG. 19a and illustrating the catheter rotated 45° from the orientation of FIG. 19a;

FIG. 20b is a radial cross-section view taken along lines 20b—20b of FIG. 20a;

FIG. 21a is a side-elevation view illustrating the catheter rotated 90° from the orientation of FIG. 19a;

FIG. 21b is a radial cross-section view taken along lines 21b—21b of FIG. 21a;

FIG. 22a is a side elevation view illustrating the catheter rotated 135° from the orientation of FIG. 19a;

FIG. 22b is a radial cross-section view taken along lines 22b—22b of FIG. 22a;

FIG. 23a is a side elevation view illustrating the electrode rotated 180° from the orientation of FIG. 19a;

FIG. 23b is a radial cross-section view taken along lines 23b—23b of FIG. 23a;

FIG. 24a is a side elevation view similar to FIG. 5 and illustrating an embodiment wherein the electrode is energized through two conductors;

FIG. 24b is an enlarged side-elevation view of the electrode illustrated in FIG. 24;

FIG. 25 is a side-elevation view of a semi-bipolar embodiment of the catheter;

FIG. 26 is an enlarged view of the distal end of the catheter illustrated in FIG. 25;

DESCRIPTION OF PREFERRED EMBODIMENTS AND BEST MODE OF THE INVENTION

Figure 1:
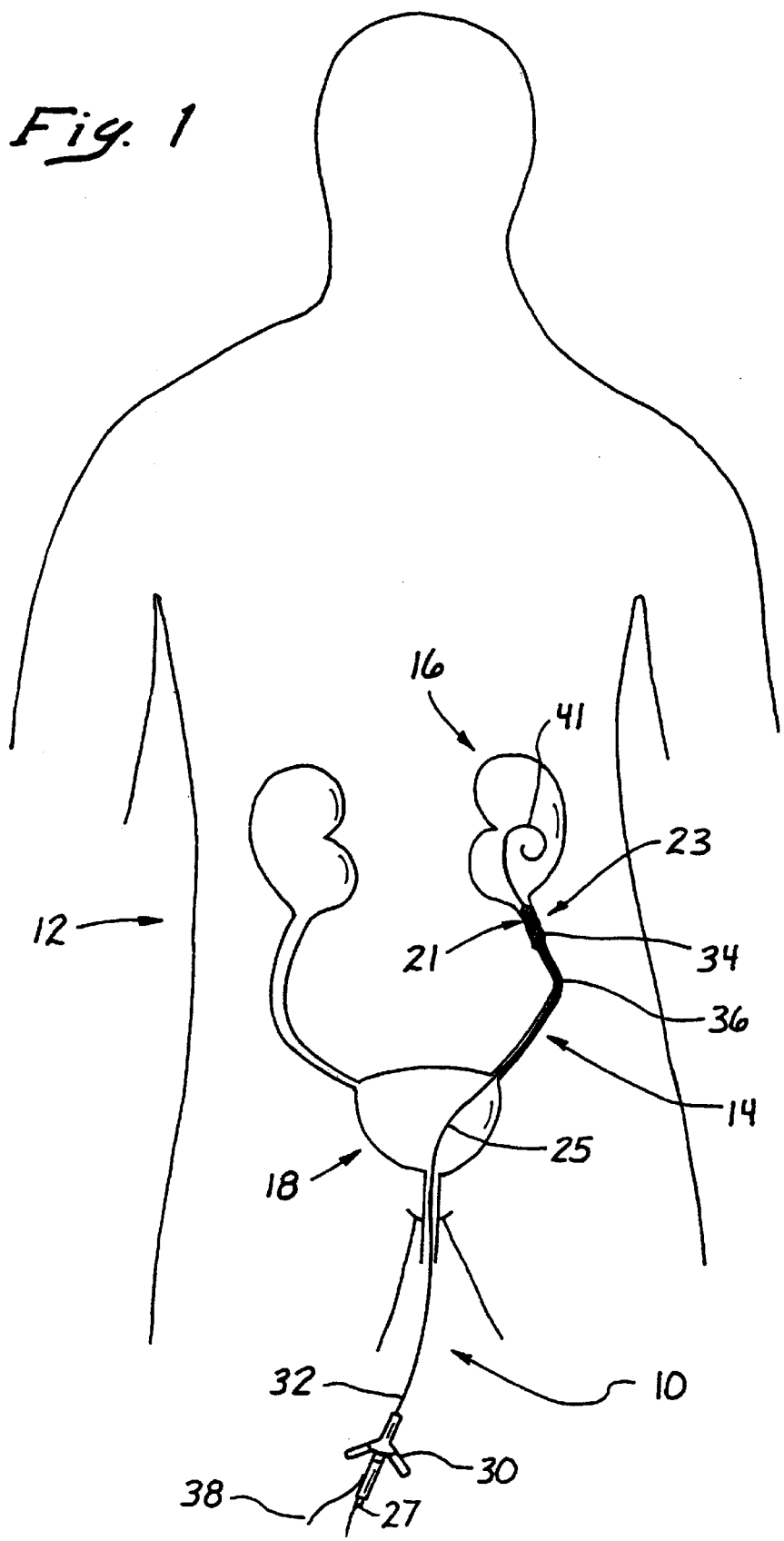
FIG. 1 is a top-plan view of a patient illustrating operative placement of an electrosurgical balloon catheter in the upper pelvic junction between a kidney and a bladder of the patient.

A catheter is illustrated in FIG. 1 and designated generally by the reference numeral 10. The catheter 10 is illustrated to be operatively disposed in a patient 12 having a ureter 14 extending between a kidney 16 and a bladder 18. The catheter 10 is adapted to increase the patency of the ureter 14, particularly at the upper pelvic junction 21 which is commonly occluded by strictures 23.

The catheter 10 typically includes an elongate tube 25 having a lumen 27 extending through a hub 30 at a proximal end 32, and an electrode assembly 34 at a distal end 36. The electrode assembly 34 is electrically energized through a conductor 38 at the proximal end 32. Operative placement of the catheter 10 can be facilitated by a guide catheter or a guidewire 41.

FIG. 2 shows an enlarged view of the upper pelvic junction 21 with the electrode assembly 34 including a balloon 45, a sheath 47 extending over the balloon 45, and an electrode 50. These elements are perhaps more easily identified in the radial cross-section view of FIG. 3.

The side elevation views of FIGS. 4 and 5 illustrate the electrode assembly 34 in a low-profile state and a high-profile state, respectively. In the low-profile state of FIG. 4, the catheter 10 is adapted for insertion through the bladder 18 and into the ureter 14. Once the catheter 10 is operatively disposed, the balloon 45 is expanded, for example by inflation, to a high-profile state, as illustrated in FIG. 5. In the high-profile state, as illustrated in FIG. 2, the balloon 45 functions to carry the electrode 50 radially outwardly into proximity with the strictures 23 to facilitate the electrosurgical effect. The balloon 45 in the high-profile state also functions to tension the walls of the ureter 14 so that the ureter 14 expands as the strictures 23 are cut by the electrode 50. Any potential for bleeding is inhibited by the tamponade effect of the inflated balloon 45.

Figure 6:
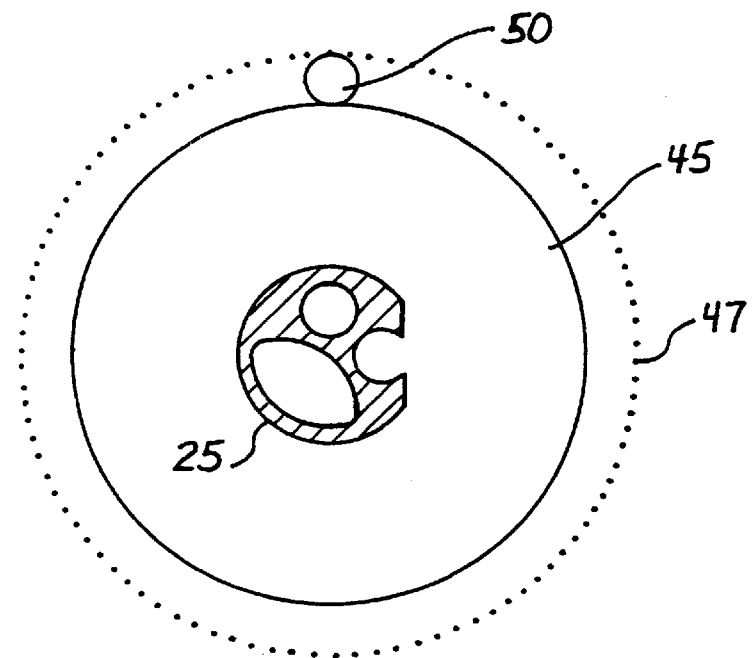
FIG. 6 is an enlarged radial cross-section view taken along lines 6—6 of FIG. 5.
Figure 7:
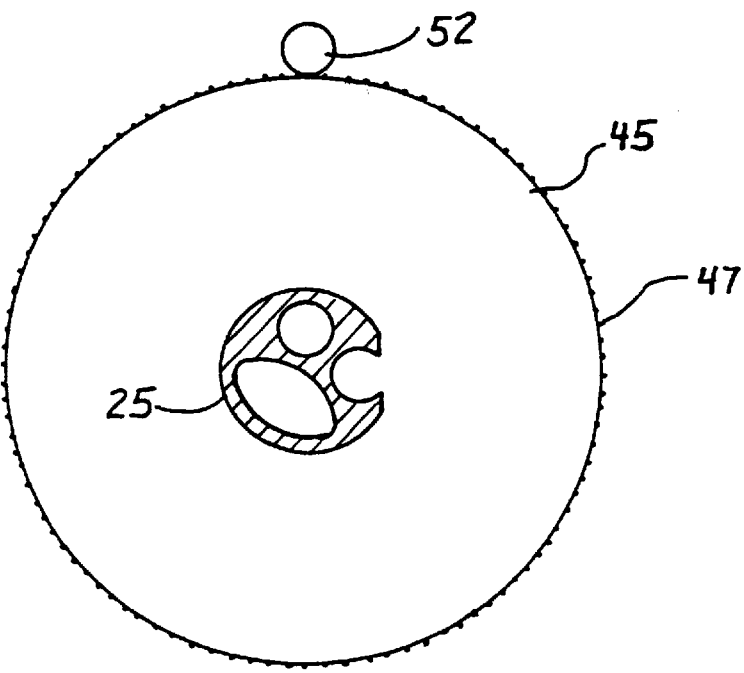
FIG. 7 is an enlarged radial cross-section view taken along lines 7—7 of FIG. 5.

The cross-section views of FIGS. 6 and 7 illustrate a preferred embodiment wherein the electrode 50 exits the tube 25 exteriorally of the balloon 45, but interiorly of the sheath 47. Portions of the electrode 50, designated generally by the reference numeral 52, extend through the sheath where they are exposed axially along the outer surface of the sheath 47.

The side elevation views of FIGS. 4 and 5 are perhaps best suited to disclose another feature of the present invention. In these figures, the balloon has ends which are fixed to the tube 25 by windings 54, 56. With the windings 54, 56 fixed to the tube, axial movement of the balloon 45 is inhibited, so that expansion of the balloon 45 is limited generally to the radial direction. By comparison, the ends of the sheath 47 are fixed to bushings 58, 61 which are separated by a central section 63 are free to float axially along the tube 25. Thus, the bushings 58 and 61 have inside diameters which are greater than the outside diameter of the tube 25. In the low-profile state illustrated in FIG. 4, the bushings 58 and 61 have a maximum distance of separation as the length of the sheath 47 increases in response to radial compression of the balloon 45 and the sheath 47.

As the balloon 45 expands radially outwardly, it carries with it the central section 63 of the sheath 47. This radial expansion of the sheath 47 draws the floating bushings 58, 61 together reducing their distance of separation. In the high-profile state illustrated in FIG. 5, the floating bushings 58, 61 of the sheath 47 abut the fixed windings 54, 56 of the balloon 45. At this point, the distance separating the bushings 58, 61 can no longer be reduced. With the ends of the sheath 47 limited against further proximal movement, the maximum diameter of the sheath 47 is fixed to a diameter which dictates the predetermined high-profile state of the electrode assembly 34. Note that this also fixes the maximum radial separation of the catheter tube 25 and the exposed portions 52 of the electrode 50.

Figure 8:
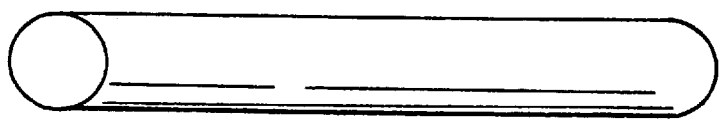
FIG. 8 is a perspective view of an electrode conductor of the prior art having a circular cross-section.

Theoretically, the electrode 50 and the conductor 38 should be sized and configured to conduct the maximum amount of current through the conductor 38 to the electrode 50, and then to provide an electrode 50 of minimum surface area in order to increase the current density at the electrode 50. Of course, there are maximum size and flexibility constraints on the conductor 38, as well as strength and integrity constraints on the electrode 50 which place practical demands on these theoretical considerations. In the past, both the conductor 38 and the electrode 50 have been formed of wires having a circular cross-section as illustrated in FIG. 8. Within the practical constraints noted, the round conductor 38 has been chosen with a maximum diameter and the round electrode 50 has been chosen with a minimum diameter. In U.S. Pat. No. 5,628,746, Applicant discloses and claims a concept for providing a relatively large electrode wire with surface insulation that is removed to expose only a very small area of the electrode. This has had the same effect of providing a high-current density, but has enabled use of a relatively large electrode to do so. As a result, electrodes as large as the associated conductors have been used in the past. When the practical constraints on the conductor have been maximized, embodiments providing for a relatively large electrode tapering to a relatively small conductor have been used.

Against this background of evolution, it has now been found that electrical energy passing through a conductor at radio frequencies tends to flow along the outer surface of the conductor. This is referred to as the "skin effect." Taking this phenomena into account, the conductor 38 and electrode 50 of the present invention can be provided with a generally non-circular shape in axial cross-section. This shape can take the form illustrated in FIG. 9, for example, or can naturally result from a stranded conductor 38, as illustrated in FIG. 10. In this embodiment, the conductor 38 electrode 50 include at least two elongate elements 70, 72 which are stranded, such as woven, braided, or twisted, along an axis 75 from the proximal end of the conductor 38 through to the distal end of the electrode 50. These elements 70, 72 may have a circular cross-section, as illustrated in FIG. 10, or may also be provided with a non-circular cross-section maximizing their individual surface areas.

Figure 11:
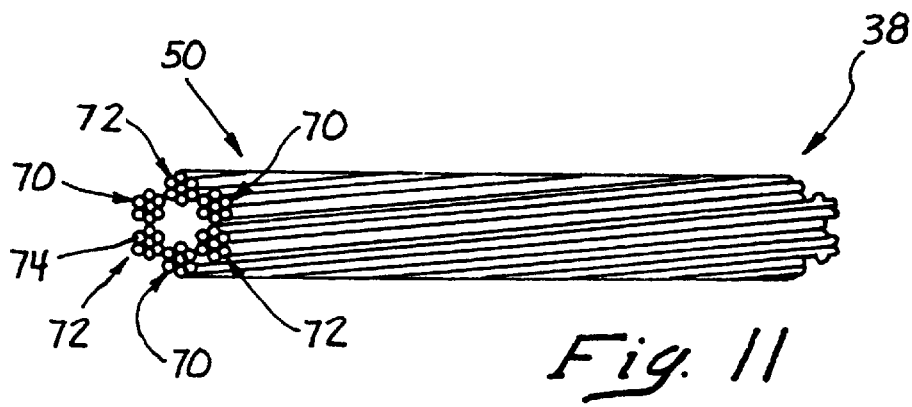
FIG. 11 is a perspective view of a further embodiment of the conductor wherein each element is comprised of separate fibers and the elements define the electrode with a generally hollow configuration.

Another embodiment illustrated in FIG. 11 provides an even further increase in the surface area of the conductor 38 and electrode 50. In this embodiment, each of the elements 70, 72 is formed of a plurality of fibers 74. These fibers 74 are twisted together to form the individual elements 70, 72, which are further twisted together to form the conductor 38 and electrode 50. In the FIG. 11 embodiment, the resulting conductor 38 and electrode 50 have a generally hollow configuration so that none of the elements, such as the elements 70 and 72, extend along the axis of the conductor 38. By comparison, the conductor 38 and electrode 50 illustrated in FIG. 12 include a further element 76 which extends along the axis 75, with the remaining elements 70, 72 twisted around the core element 76.

Figure 9:
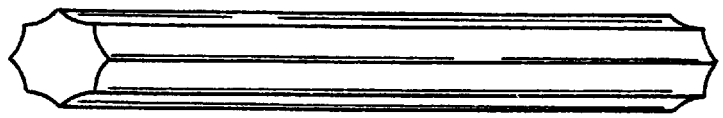
FIG. 9 is a perspective view of one embodiment of an electrode conductor of the present invention having a non-circular cross-section.
Figure 10:
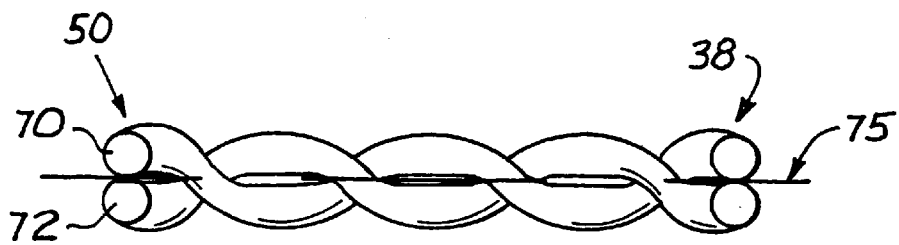
FIG. 10 is a perspective view of a further embodiment of the conductor comprising discrete elements stranded to form the electrode.
Figure 12:
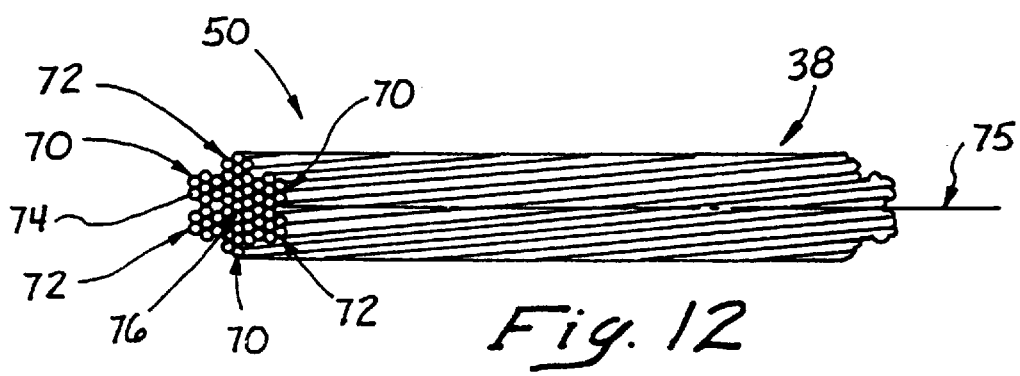
FIG. 12 is a perspective view of a further embodiment of the electrode similar to FIG. 11, but having a generally solid, non-hollow configuration.

From these embodiments illustrated in FIGS. 9–12, it will be apparent that an increased surface area can be achieved generally with any non-circular cross-section. In FIG. 9, the conductor 38 is solid and the outer surface is sculptured to provide the increased surface area. In the embodiment of FIG. 10, multiple elements are stranded to provide the increased surface area. The cross-section of these individual elements can also be non-circular. Importantly, there can be two or more elements, such as the elements 70, 72, in this embodiment. The more elements, the greater the surface area. This is more apparent from the FIG. 11 embodiment which includes six elements, such as the elements 70, 72. To further increase the surface area, each of these elements is formed from individual fibers which can also be provided with other than round cross-sections. Whether the cross-section of the connector 38 is hollow, as illustrated in FIG. 11, or generally solid, as illustrated in FIG. 12, it is apparent that the surface area of the conductor 38 is greatly increased over the generally cylindrical circular cross-section associated with the conductors and electrodes of the prior art.

Figure 13:
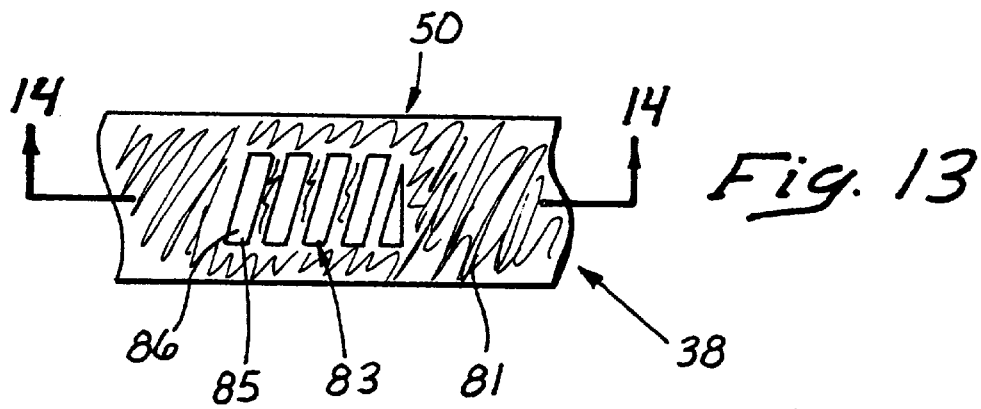
FIG. 13 is a plan view of an electrode having at least one conductor element formed in a spiral configuration, and a coating of insulation with portions removed to form discrete windows for element exposure.
Figure 14:
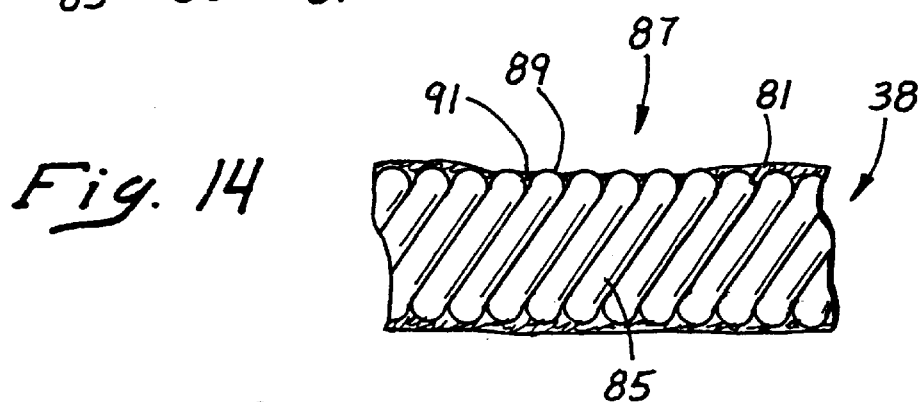
FIG. 14 is an axial cross-section view taken along lines 14—14 of FIG. 13.

Turning now to the electrode 50 illustrated in FIG. 13, it will be apparent that the conductor 38 with a spiraled configuration can offer significant advantages when covered with an insulation 81. When this insulation is removed, individual windows 83 are formed and exposed portions 86 of the convolutions 85 are individually exposed. This is perhaps best illustrated in the axial cross-section view of FIG. 14 where the insulation 81 is removed in an area designated generally by the reference numeral 87. From this view it can be seen that the outer surface of the convolutions 85 forms peaks 89 alternating with valleys 91. When the insulation is removed from the area 87, it tends to remain in the valleys 91 so that only the peaks 89 and the convolutions 85 are exposed. This produces the individual windows 83 and the discreet, exposed convolutions 85 of the conductor 38, as illustrated in FIG. 13.

It should be noted that with this window configuration, the exposed area of the conductor 38 can be even further reduced, greatly increasing the current density of the electrode 50. In the past, the entire conductor was exposed within the area of the removed insulation 87. In the window embodiment, as illustrated in FIG. 13, the much smaller area of exposure can provide a substantial increase in current density.

Figure 15:
FIG. 15 is a top-plan view similar to FIG. 13 with the windows oriented in a radial configuration.
Figure 16:
FIG. 16 is a top-plan view similar to FIG. 13 with the windows oriented in an axial configuration.
Figure 17:
FIG. 17 is a top-plan view similar to FIG. 13 with the windows oriented in a spiral configuration.

From these views, it can be appreciated that the particular surface configuration associated with the conductor 83, and the pattern for removing the insulation 81, can provide the windows 83 and the exposed portions 86 of the conductor 38 with different spatial relationships. For example, in FIG. 15, the windows 83 and exposed portions 86 have a curved, radial relationship. In FIG. 16, the windows 83 and exposed portions 86 have a generally straight, axial relationship. Finally, in FIG. 17, the windows 83 and exposed portions 86 are curved with a spiral relationship.

A further embodiment of the invention is illustrated in FIG. 18 wherein the conductor 38 is formed of multiple elements as taught generally with reference to FIGS. 10, 11. These elements 70, 72 are individually provided with an insulation coating 101 FIG. 18, which enables them to be individually and separately energized or controlled. While this control may provide for variations in the magnitude of energy, it will typically be a matter of timing that energy at each window 83. Thus, the individual and discrete windows 83 and the insulation 81 can be separately, and perhaps progressively, energized to further maximize the current density as the elements 70, 72 are selectively energized at the associated windows 83.

A further embodiment of the invention is illustrated in FIGS. 19a–23a and their associated cross-sectional views in FIGS. 19b–23b. In this embodiment, the balloon 45 is provided with a metal coating 105, but only along a portion of its radial surface. For example, in the views illustrated, the metal coating 105 extends only 180° around the circumference of the balloon 45. This greatly aids in the radial orientation of the balloon 45 and, of course, facilitates operative disposition of the electrode 50. Radiopague markers 107 can also be provided to further enhance axial location of the catheter 10.

Viewing the catheter 10 fluoroscopically will present a side-elevation view such as those associated with FIGS. 19a–23a. From these fluoroscopic observations, the surgeon will attempt to rotate the catheter 10 along its axis in order to accurately place the electrode 50 in the desired radial disposition. By providing the balloon 45 with the metalized coating 105, a sharp line of demarcation 109 is now apparent along the entire length of the balloon 45. If the surgeon requires an upper placement of the electrode 50, the catheter 10 can merely be turned on its axis until the fluoroscopic view of FIG. 19a is achieved. Different fluoroscopic views can be sought to achieve other preferred positions for the electrode 50. For example, progressive 45° turns in a clockwise direction are illustrated in the side-elevation views of FIGS. 19a–23a.

It should be apparent from these views that the metalized coating 105 greatly facilitates operative disposition of the electrode 50. Although a semi-cylindrical placement of the coating 105 is illustrated in this embodiment, many other shapes of the coating 105 can also be relied on to facilitate radial placement of the electrode 50. Fluoroscopically, the embodiment illustrated in FIGS. 19a–23a provides the longest line of demarcation 109 and perhaps the greatest visual indication of electrode orientation. It should also be noted that the metalized coating, such as the coating 105 on the balloon 45, can also be applied to the sheath 47 individually or in combination with the balloon 45.

As previously discussed, it is desirable to maximize the magnitude of radio frequency current which can be delivered to the electrode 50. In the past, the electrode 50 has been provided with a proximal end 110 and a distal end 112. The proximal end 112 has been coupled to the connector 38 in order to energize the electrode 50. More typically, the metal core of the electrode 50 has been formed integral with the conductor 38 as a mere extension of the conductor 38. The distal end 112 of the electrode 50 has been terminated in the tube 25 of the catheter 10.

In accordance with the embodiment FIG. 24, a second conductor 114 is provided which extends through the hub 30 at the proximal end 32, and is coupled to the distal end 112 of the electrode 50. The second conductor 114 provides a further path for the transmission of electrical current to the electrode 50. The resulting increase in current which can be transmitted provides a commensurate increase in current density at the electrode 50.

A semi-bipolar embodiment of the catheter 10 is illustrated in FIG. 25. In this embodiment, either or both the balloon 45 and the sheath 47 have a metallic outer surface 118 which provides a large area of contact with the body material, such as the strictures 23 (FIG. 1), which define the body conduit. In this embodiment, the conductor 38 is connected to the electrode 50 in the manner previously discussed. A second conductor 121, also emanating from the hub 30, is connected to the metallic surface 118. With the electrosurgical signal introduced across the conductors 38 and 121, the catheter 10 tends to function in a bipolar mode with current passing from the relatively small surface area of the electrode 50 to the relatively high surface area of the metallic surface 118. This configuration is bipolar in that both of the poles of the electrosurgical circuit are carried by the catheter 10. The configuration is monopolar to the extent that one of the poles presents a surface area so large that the current density at this pole has no effect upon the tissue of the patient. This embodiment is referred to herein as semi-bipolar.

Figure 27:
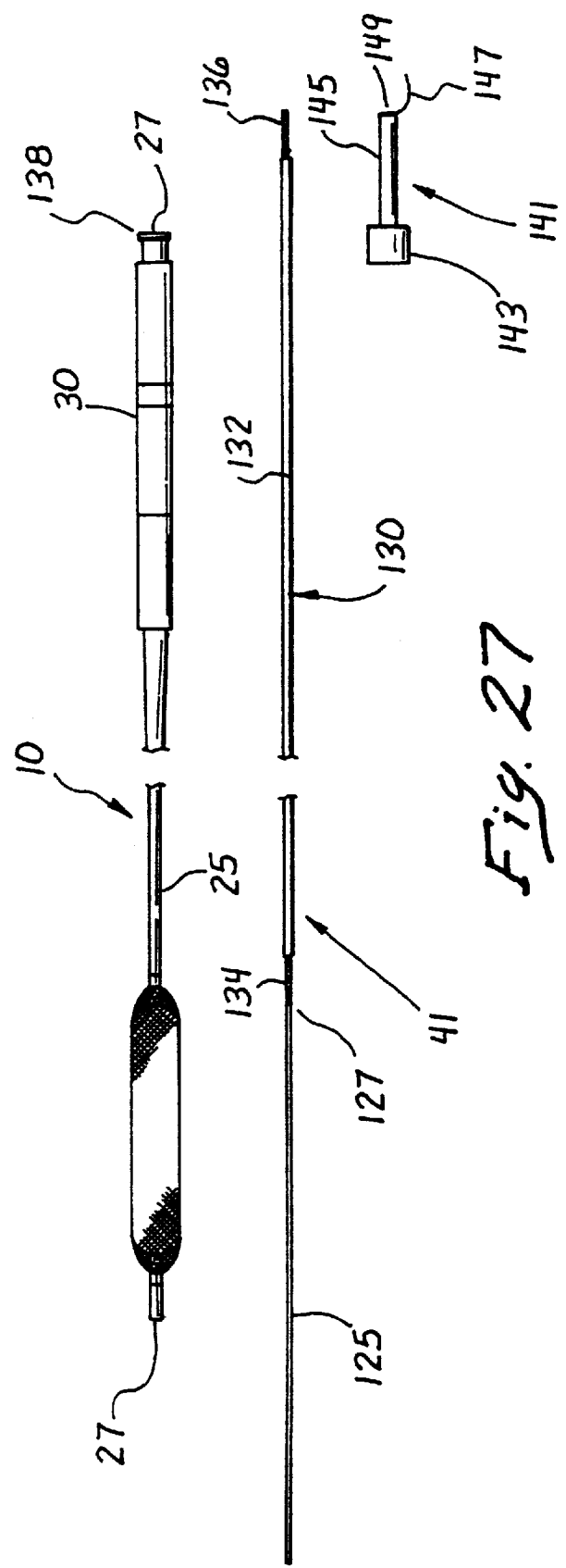
FIG. 27 is an assembly view of a catheter system wherein a guidewire is used to energize the electrode of the catheter.
Figure 28:
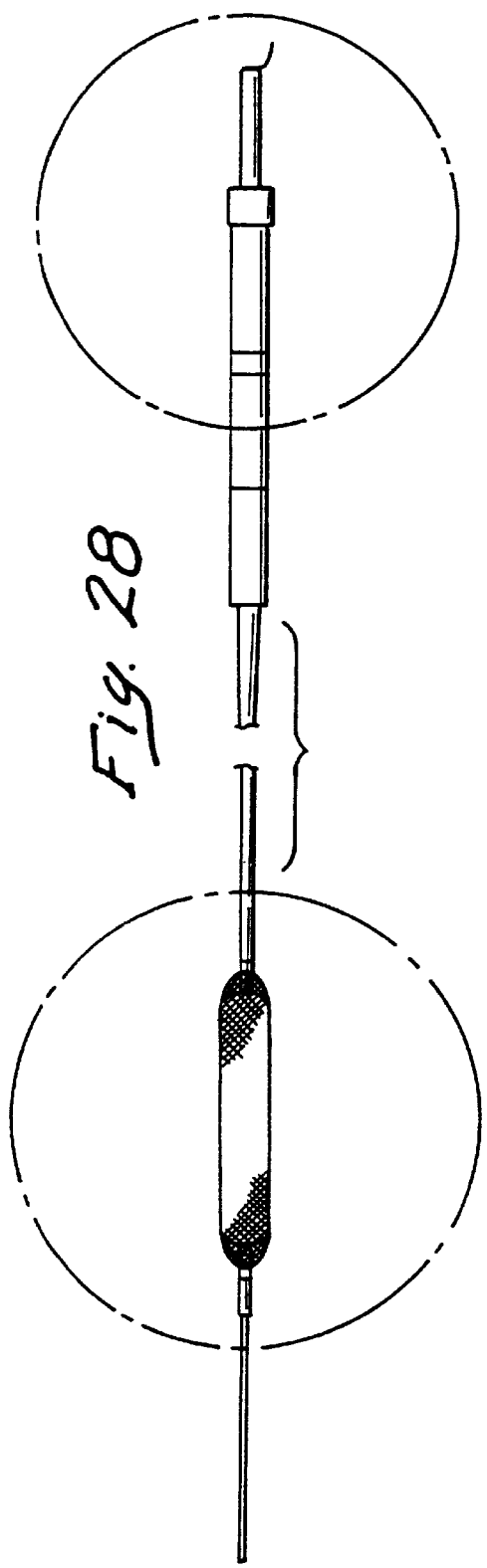
FIG. 28 is an assembled view of the elements illustrated in FIG. 27.

In order to facilitate insertion of the catheter 10, it is always of interest to minimize the cross-sectional area of the tube 25. This is accomplished in a preferred embodiment illustrated in FIGS. 27–29, where the tube 25 has but a single lumen 27 (FIG. 3). This lumen 27, which can be used to inflate the balloon 45, is primarily sized and configured to receive the guidewire 41.

The guidewire 41 in this case is especially constructed with a non-conductive distal portion 125 coupled at a junction 127 to a conductive proximal portion 130. The conductive proximal portion 130 is covered generally centrally with insulation 132 leaving exposed a distal patch 134 near the junction 127, and a proximal patch 136 at the proximal end of the guidewire 41.

At the proximal end of the catheter 10, the hub 30 can be provided with a threaded male fitting 138 which is adapted to receive the guidewire 41. A complementary cap 141 includes a female fitting 143, adapted to receive the fitting 138, and a tube 145 which extends proximally axially from the fitting 143. A conductor 147 is molded into a closed end 149 of the tube 145.

In operation, the guidewire 41 is inserted into the body conduit, such as the ureter 14, in a manner well-known in the art. The catheter 10 is then threaded over the proximal end of the guidewire 41 and pushed distally toward its operative position until the proximal end of the guidewire 41 is exposed at the hub 30. At this point, the cap assembly 141 is moved over the proximal end of the guidewire 41 until the proximal patch 136 achieves electrical conductivity with the conductor 147. Holding the hub 30 in one hand, and moving the cap assembly 141 forces the guidewire 41 distally relative to the catheter, but also brings the female fitting 143 into an abutting relationship with the male fitting 138. At this point, the cap assembly 141 can be tightened to the male fitting 138 to hold the catheter 10 and guidewire 41 in a fixed axial relationship. This relationship is facilitated by a radial seal 152 in the embodiment of FIG. 29.

Figure 29:
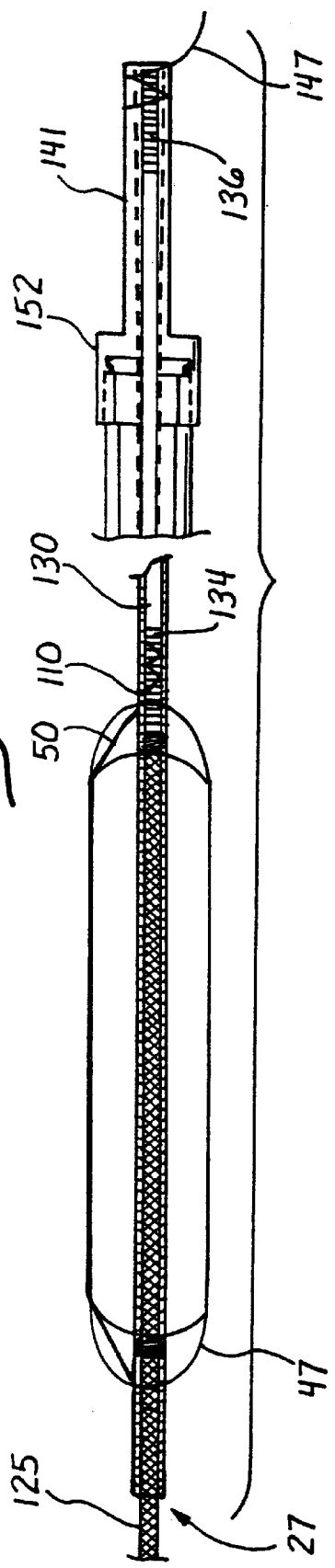
FIG. 29 is a radial cross-section view of the assembled elements of FIG. 28 illustrating the conduction of electrosurgical energy from the proximal end of the guidewire to the electrode of the catheter.

At the distal end of the catheter 10, the electrode 50 is provided with a proximal end 110 that is foreshortened, but exposed within the lumen 27 in proximity to the sheath 47. The exact location of the proximal end 110 of the electrode 50 is predetermined relative to the hub 30. This known distance can be used to locate the distal patch 134 of the conductor 130 on the guidewire 41 so that complete assembly of the guidewire 41 and catheter 10, as illustrated in FIG. 29, brings the proximal end 110 of the electrode 50 into electrical contact with the distal conductive patch 134. With these structural relationships, electrosurgical energy applied to the conductor 147 at the proximal end of the cap assembly 141 will pass through the conductor proximal portion 130 to the conductive patch 134. This energy will then be transferred to the distal end 110 and into the electrode 50.

In this manner, the guidewire 41 can be used to energize the electrode 50, thereby eliminating the need for any energizing conductor such as the conductor 38 (FIG. 5). It will be noted that, with the guidewire 41 thus configured, there are no conductive elements of the guidewire 41 which extend beyond the distal end of the catheter 10. Also, although the insulation 132 over the conductor portion 130 is provided in a preferred embodiment, this may be eliminated in another embodiment since the conductor 130 is effectively insulated by the tube 25 of the catheter 10. A further advantage associated with this system relates to the axial placement of the catheter 10. Once the guidewire 41 is axially oriented with the junction 127 disposed at a predetermined position, location of the catheter 10 and associated electrode 50 is fixed along the length of the guidewire 41. Not only is the catheter 10 fixed to the guidewire 41 at this preferred location, but the electrode 50 is only energized at this predetermined location along the guidewire 41.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

What is claimed is:

1. A catheter adapted to increase the patency of a body conduit, comprising:

an elongate tube having an axis extending between a proximal end and a distal end;

a balloon disposed at the distal end of the tube and having properties for being expanded to a high-profile state and for being deflated to a low-profile state;

a sleeve being disposed over the balloon in a generally cylindrical configuration and having a pair of ends disposed on opposing sides of a central section;

the ends of the sleeve disposed to engage the tube with the central section of the sleeve disposed circumferentially of the balloon;

an electrode having portions disposed outwardly of the sleeve, the electrode having properties for being electrosurgically energized to incise materials defining the body conduit when the balloon is in the high-profile state; and at least one of the ends of the sleeve having a floating relationship with the tube to facilitate the generally cylindrical configuration of the sleeve when the balloon is in the high-profile state.

2. The catheter recited in claim 1 wherein the sleeve has non-distendable properties for maintaining the balloon in its high-profile state at a predetermined diameter.

3. The catheter recited in claim 2:

wherein the sleeve ends are free to float relative to each other between positions displaced by an axial distance of separation; and the predetermined diameter of the balloon in the high-profile state is dependent upon the axial distance of separation of the sleeve ends.

4. The catheter recited in claim 3, wherein:

the balloon has balloon ends fixed to the tube at axially spaced locations; and the axial distance of separation of the sleeve ends is dependent upon the axially spaced location of the balloon ends.

5. The catheter recited in claim 1 wherein the tube in proximity to the balloon has an outer diameter and the ends of the sleeve have a fixed diameter greater than the outer diameter of the tube to facilitate axial flotation of the sleeve ends relative to the tube.

6. The catheter recited in claim 1 wherein the sleeve is formed of discrete elements interwoven to form a fabric.

7. The catheter recited in claim 6 wherein the electrode is interwoven into the sleeve.

8. The catheter recited in claim 6 wherein the electrode forms one of the elements in the woven fabric of the sleeve.

9. The catheter recited in claim 1 wherein the sleeve includes at least one of a thermoplastic and a thermoset material.

10. The catheter recited in claim 1, further comprising:

a coating disposed between the electrode and the sleeve and having properties for insulating the sleeve against the electrode.

11. A catheter adapted to increase the patency of a body conduit, comprising:

an elongate tube having an axis extending between a proximal end and a distal end;

a balloon disposed at the distal end of the tube and having properties for being expanded from a low-profile state to a high-profile state;

an electrode disposed outwardly of the balloon and having properties for being electrosurgically energized to incise the material forming the body conduit; and the electrode being formed of a plurality of elements stranded to form the electrode and to provide the electrode with an outer surface having peaks and valleys, the valleys being unexposed and the peaks being exposed only in a predetermined cutting pattern.

12. The catheter recited in claim 11 wherein each of the stranded elements includes multiple fibers.

13. The catheter recited in claim 11, further comprising:

an insulation disposed over the stranded electrode; and the insulation including portions defining a plurality of windows each exposing an associated one of the peaks of the stranded electrode in the predetermined cutting pattern.

14. The catheter recited in claim 13 wherein the predetermined cutting pattern is one of an axial line, a radial line, and a spiral line.

15. The catheter recited in claim 11 further comprising:
a spring coupled to the electrode to bias the electrode against the balloon in both the low-profile state and the high-profile state.

16. A catheter adapted to increase the patency of a body conduit, comprising:
an elongate tube having an axis extending between a proximal end and a distal end;
a balloon disposed at the distal end of the tube and having properties for being expanded from a low-profile state to a high-profile state;
an electrode disposed outwardly of the balloon and having properties for being electrosurgically energized to incise the material forming the body conduit;
the electrode being formed of a plurality of elements stranded to form the electrode;
a first conductor disposed within the tube and providing electrical conductivity between the proximal end of the tube, and one of the proximal end and the distal end of the electrode, and
a second conductor disposed within the tube and providing electrical conductivity between the proximal end of the tube and the other of the proximal end and the distal end of the electrode.

17. The catheter recited in claim 16 wherein one of the first conductor and the second conductor is a guidewire.

18. A catheter adapted to increase the patency of a body conduit, comprising:
an elongate tube having an axis extending between a proximal end and a distal end;
a balloon disposed at the distal end of the tube and having properties for being expanded to a high-profile state and for being deflated to a low-profile state;
a sleeve formed of discrete elements interwoven to form a fabric and being disposed over the balloon, the sleeve having a pair of ends disposed on opposing sides of a central section;
the ends of the sleeve disposed to floatingly engage the tube with the central section of the sleeve disposed circumferentially of the balloon;
the sleeve having properties for radially compressing the balloon when the balloon is in the low-profile state; and
an electrode having portions disposed outwardly of the sleeve, the electrode having properties for being electrosurgically energized to incise materials defining the body conduit when the balloon is in the high-profile state.

19. The catheter recited in claim 18 wherein the electrode is interwoven into the sleeve.

20. The catheter recited in claim 18 wherein the electrode forms one of the elements in the woven fabric of the sleeve.

\* \* \* \* \*